(12) United States Patent
Simon et al.

(10) Patent No.: US 8,642,769 B2
(45) Date of Patent: Feb. 4, 2014

(54) PEPERIDINE-FLAVAN ALKALOID COMPOUNDS DERIVED FROM AFRICAN HERB TEA KINKELIBA AS ANTI-DIABETIC AGENTS

(76) Inventors: James E. Simon, Princeton, NJ (US); Qingli Wu, Annandale, NJ (US); Cara Welch, Washington, DC (US)

( * ) Notice: Subject to any disclaimer, the term of this patent is extended or adjusted under 35 U.S.C. 154(b) by 0 days.

(21) Appl. No.: 13/695,911

(22) PCT Filed: May 3, 2011

(86) PCT No.: PCT/US2011/034966
§ 371 (c)(1),
(2), (4) Date: Jan. 30, 2013

(87) PCT Pub. No.: WO2011/140066
PCT Pub. Date: Nov. 10, 2011

(65) Prior Publication Data
US 2013/0143921 A1  Jun. 6, 2013

Related U.S. Application Data

(60) Provisional application No. 61/330,498, filed on May 3, 2010.

(51) Int. Cl.
*C07D 401/00* (2006.01)

(52) U.S. Cl.
USPC .......................... 546/196; 514/320

(58) Field of Classification Search
USPC .......................... 546/196; 514/320
See application file for complete search history.

(56) References Cited

U.S. PATENT DOCUMENTS 3,711,485 A  1/1973  Ferrari et al.

OTHER PUBLICATIONS

Ahond et al Bulletin de la Societe Chimique de France 1984, pp. 41-45—abstract.*
Welch. Chemistry and Pharmacology of Kinke'Liba (Combretum Micranthum), A West African Medicinal Plant. Dissertation submitted to the Graduate School-New Brunswick Rutgers, The State University of New Jersey in partial fulfillment of the requirements for the degree of Doctor of Philosophy, Jan. 2010; p. 39, para 1 to p. 40, para 1; p. 59, para 1 to 60, para 2; p. 119, para 2 to p. 120, para 2 Downloaded from http://hdl.rutgers.edu/1782.21rucore10001600001.ETD.000052288.
Dembinska-Kiec et al. Antioxidant phytochemicals against type 2 diabetes. British Journal of 30-32 Nutrition, 2008, vol. 99, E-Suppl, 1, pp. ES109-ES117; entire document Downloaded_from http://journals.cambridge.org/.
Balde et al. Herbal medicine and treatment of Diabetes in Africa: an example from Guinea. Diabetes Metab, 2006, vol. 32, pp. 171-175; p. 172, para 5 to p. 174, para 3, Table III Downloaded from http://www.em-consulte.com/article/80474.

* cited by examiner

*Primary Examiner* — John Mabry
(74) *Attorney, Agent, or Firm* — Fox Rothschild LLP; Gerard P. Norton; Wansheng Jerry Liu

(57) ABSTRACT

This invention provides the methods of separation and identification of a novel type of piperidine flavan alkaloids from an African herbal tea, the leaves of *Combretum micranthum* commonly known as kinkeliba, and the procedures for preparing the total piperidine flavan alkaloids (TPFA). In particular, this invention relates to the use of the plant extract that may contain TPFA as anti-diabetic agents in treatment of metabolic disorders and other applications related to this new chemical structure and derivatives thereof.

17 Claims, 6 Drawing Sheets

(1) kinkéloid A₁: $R_1$ = 2-piperidinyl, $R_2, R_3, R_4, R_5$ = H
  kinkéloid A₂: $R_2$ = 2-piperidinyl, $R_1, R_3, R_4, R_5$ = H (2) kinkéloid B₁: $R_1$ = 2-piperidinyl, $R_2, R_3, R_5$ = H, $R_4$ = OH
  kinkéloid B₂: $R_2$ = 2-piperidinyl, $R_1, R_3, R_5$ = H, $R_4$ = OH (3) kinkéloid C₁: $R_1$ = 2-piperidinyl, $R_2, R_3$ = H, $R_4, R_5$ = OH
  kinkéloid C₂: $R_2$ = 2-piperidinyl, $R_1, R_3$ = H, $R_4, R_5$ = OH (4) kinkéloid D₁: $R_1$ = 2-piperidinyl, $R_2, R_3, R_4, R_5$ = OH
  kinkéloid D₂: $R_2$ = 2-piperidinyl, $R_1, R_3, R_4, R_5$ = OH Exact Mass: 222.1120

PEPERIDINE-FLAVAN ALKALOID COMPOUNDS DERIVED FROM AFRICAN HERB TEA KINKELIBA AS ANTI-DIABETIC AGENTS

CROSS REFERENCE TO RELATED APPLICATIONS

This application is the U.S. National Phase of International Patent Application Serial No. PCT/US11/34966, filed May 3, 2011, which claims priority of U.S. Provisional Application No. 61/330,498, filed on May 3, 2010. The contents of the foregoing applications are incorporated herein by reference in their entireties.

FIELD OF THE INVENTION

The present invention relates to the separation and identification of a series of novel type piperidine flavan alkaloids, Kinkéloids A, B, C, and D (FIG. 1) from an African herb tea, the leaves of *Combretum micranthum* (fam. Combretaceae), commonly known as kinkéliba, and the procedures for preparing the total piperidine flavan alkaloids (TPFA). Particularly, this invention relates to use of these compounds for health and cosmetic applications including but not limited to anti-diabetic bioactive properties of these compounds.

BACKGROUND OF THE INVENTION

Botanical Description.

The Combretaceae family is composed of 20 genera and some 600 species and it is well represented in South and South West Africa and Botswana. The family is spread throughout most tropical countries. Five genera are found in Southern and Western Africa, four of which are tree species. *Combretum* is the largest genus with 350 spp. and is widely used in traditional African medicine. *Combretum micranthum* is a bushy shrub or creeper that can grow up to 20 m in height. The leaves are opposite, ovale acuminate and the flowers are born as axillary cluster on scaly stalks, with a whitish corolla and ferruginous scales covering the calyces. The flowers typically produce nectar and attract insects, birds, and small mammals [1]. *C. micranthum* is common on cultivated ground, throughout the continent, but it appears to be dominant in Sub-Saharan Africa, from Sudan to Nigeria, from Gambia to Congo [1].

Traditional Uses of Combretaceae.

Traditional medicines from around the world serve as potential new sources of bioactive molecular entities and promising directions for therapeutic investigation. These medicines derive from indigenous herbs, teas, spices and plants used singly or in combination as long-established healing tonics including drinks, poultices, or steam treatments. One such "drink of health" is kinkéliba tea, brewed from the kinkéliba leaves (*C. micranthum*) found in the African savannah regions of Senegal, Burkina Faso, and Mali. Among the *Combretum* plants, a number of bioactivities have been discovered including anti-inflammatory activity from *C. kraussii* and *C. erythrophyllum*; antimicrobial activity from *C. imberbe, C. molle, C. fragrans, C. kraussi*, and *C. woodii*; and anti-cancer activity from *C. nigricans* and *C. caffrum* which produced the combretastatins, a group of anti-tumor compounds that have progressed through to Phase II clinical trials. Kinkéliba is listed in the official Pharmacopoeia of Senegalese Traditional Medicinal and Poisonous Plants [2] and has been investigated by Bassene and Pousset, University of Cheikh Anta Diop (UCAD), Dakar, Senegal. The medicinal beverage is brewed by steeping the dried kinkéliba leaves and traditionally used for weight loss, digestion, as a diuretic and mild antibiotic, to relieve pain and, in the case of fresh leaves, the treatment of malarial fever. The herbal infusion of kinkéliba has a pleasant flavor and light brown color.

*Combretum micranthum* is an ethnomedicinal plant widely used in West Africa to treat many diseases. In traditional medicine, kinkéliba is used for the treatment of wounds and sores, guinea worm infestations, diuretic and digestion [1, 3-5]. In the fresh form, the leaves are used to reduce fevers, especially malaria fever [3, 4, 6] and as anti-inflammatory agent [7]. The bark of *C. micranthum* has high antioxidant capacity and antibacterial activity, and this is directly related to its high content of polyphenolic content [8]. It is reported that kinkéliba branches are used in local handicraft and are an important material for building material for stools, beds, tool handles, etc. [9]. A tea, made from steeping the leaves in boiling water, is a traditional tonic drink in tropical savannah countries such as Senegal, Mali and Burkina Faso and it is believed to be a general aid to weight loss and has detoxifying properties and 'healthy benefits', yet there is no specific information confirming any application nor any studies documenting its validity and/or underlying reason for its purported uses.

Kinkéliba is a native shrub that possesses well-documented medicinal properties used in West African Traditional Medicine, but has not been systematically studied to determine its origin at a molecular or chemical constituent level. Diabetes mellitus is a chronic disease that affects 180 million people worldwide, a number that is expected to double in the next 20 years (11). Type 2 diabetes, comprising approximately 90% of the cases worldwide, often develops from excess body weight and physical inactivity resulting in the body's ineffective use of insulin which creates hyperglycemia (11, 12). Despite various therapeutic agents have been developed for the treatment of this prevalent disease, there is a continuing need to discover and develop new agents or treatment methods for the disease with improved efficacy and toxicity profiles.

SUMMARY OF THE INVENTION

This present invention represents such an effort to fulfill the foregoing need based on the discovery that kinkéliba tea possesses an interesting anti-diabetic effect, which could be a combination of glucose-lowering and weight loss effects when the tea is used in a traditional manner. Because of this possible combination effect, glucose-lowering activity for TPFA was explored as an indication of antihyperglycemia or treatment of diabetes. based on a phytochemical study of kinkéliba. Thus, in one aspect the present invention is related to the compounds responsible for the bioactivity of the plants. In another aspect the present invention relates to validation of some use of the plants in traditional medicine. In another aspect the present invention sought to identify the structures of the novel bioactive compounds. In another aspect the present invention sought to exploit these new compounds for the development of new therapeutic agents for treatment of diabetes and/or other diseases or disorders.

Specifically, in one aspect the present invention provides a piperidine-flavan alkaloid compound of formula (I):

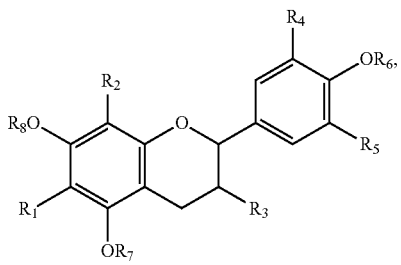

or a pharmaceutically acceptable salt thereof, wherein:
one of $R_1$ and $R_2$ is hydrogen, and the other of $R_1$ and $R_2$ is an optionally substituted 2-piperidinyl group characterized by formula (A):

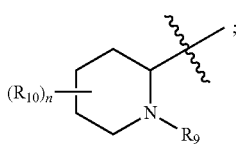

n is 0, 1, 2, or 3;
$R_3$, $R_4$ and $R_5$ are each independently selected from the group consisting of hydrogen, hydroxyl, and $C_1$-$C_4$ alkoxy;
$R_6$, $R_7$, and $R_8$ are each independently hydrogen, $C_1$-$C_4$ alkyl, or $R_{11}C(O)$—;
$R_9$ is hydrogen, $C_1$-$C_4$ alkyl, or $R_{12}C(O)$—;
$R_{10}$ at each occurrence is independently hydrogen, $C_1$-$C_4$ alkyl, or oxo (=O);
$R_{11}$ is hydrogen or $C_1$-$C_4$ alkyl; and
$R_{12}$ is hydrogen, $C_1$-$C_4$ alkyl, or $OR_{11}$.

In one embodiment, the present invention provides a piperidine-flavan alkaloid compound of formula (I), or a pharmaceutically acceptable salt thereof, wherein $R_6$ through $R_{10}$ are each hydrogen.

In another aspect the present invention provides a pharmaceutical composition derived from a species of the kinkéliba (*Combretum micranthum*) family, the composition comprising at least one piperidine-flavan alkaloid compound of formula (I).

In another aspect the present invention provides a method of separating piperidine flavan alkaloids from leaves of *Combretum micranthum* (fam. Combretaceae), commonly known as kinkéliba, comprising extracting the leaves with one or more organic solvents.

In another aspect the present invention provides a method for preparing total piperidine flavan alkaloids (TPFA) from the leaves of *Combretum micranthum*.

In another aspect the present invention provides a composition comprising an enriched TPFA extract derived from the leaves of *Combretum micranthum*.

In another aspect the present invention provides a method for treatment of a disease or condition related to glucose metabolism, comprising administering to a subject in need thereof a therapeutically effective amount of any piperidine-flavan alkaloid compound or composition thereof described above.

In another aspect the present invention provides a method for treatment of a disease or condition related to glucose metabolism, comprising administering to a subject in need thereof a therapeutically amount of TPFA derived from leaves of *Combretum micranthum* (fam. Combretaceae).

In another aspect the present invention provides use of a piperidine-flavan alkaloid compound as described above for manufacture of a medicament for treatment of a disease or condition related to glucose metabolism.

In yet another aspect the present invention provides use of a total piperidine-flavan alkaloid (TPFA) extract derived from the leaves of *Combretum micranthum* (fam. Combretaceae), for manufacture of a medicament for treatment of a disease or condition related to glucose metabolism.

DETAILED DESCRIPTION OF INVENTION

Figure 1:
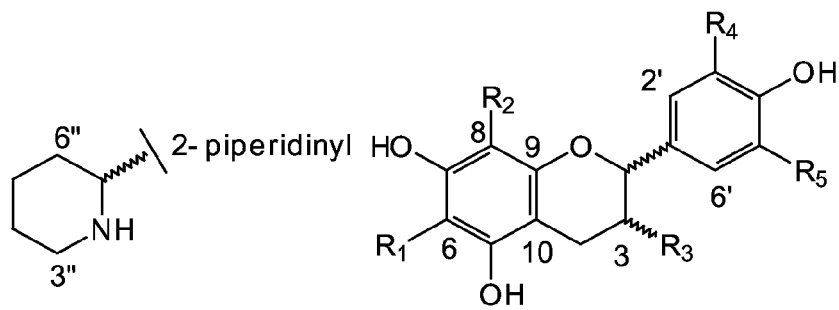
FIG. 1 illustrates the structures of the piperidine-flavan alkaloids (1-4). The structures shown are one of the several possible stereo isomers, though other isomers are present.

In one aspect the present invention provides a piperidine-flavan alkaloid compound of formula (I):

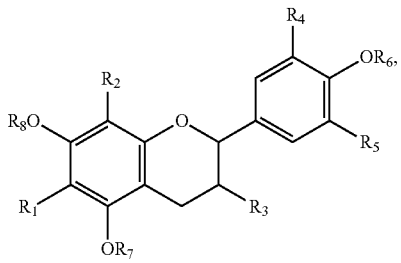

(I)

or a pharmaceutically acceptable salt thereof, wherein:
one of $R_1$ and $R_2$ is hydrogen, and the other of $R_1$ and $R_2$ is an optionally substituted 2-piperidinyl group characterized by formula (A):

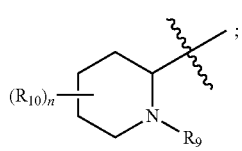

(A)

n is 0, 1, 2, or 3;
$R_3$, $R_4$ and $R_5$ are each independently selected from the group consisting of hydrogen, hydroxyl, and $C_1$-$C_4$ alkoxy;
$R_6$, $R_7$, and $R_8$ are each independently hydrogen, $C_1$-$C_4$ alkyl, or $R_{11}C(O)$—;
$R_9$ is hydrogen, $C_1$-$C_4$ alkyl, or $R_{12}C(O)$—;
$R_{10}$ at each occurrence is independently hydrogen, $C_1$-$C_4$ alkyl, or oxo (=O);
$R_{11}$ is hydrogen or $C_1$-$C_4$ alkyl; and
$R_{12}$ is hydrogen, $C_1$-$C_4$ alkyl, or $OR_{11}$.

In one embodiment, the present invention provides a piperidine-flavan alkaloid compound of formula (I), or a pharmaceutically acceptable salt thereof, wherein $R_6$ through $R_{10}$ are each hydrogen.

In another embodiment, the present invention provides a piperidine-flavan alkaloid compound of formula (I), namely kinkéloid $A_1$, or a pharmaceutically acceptable salt thereof, wherein:
$R_1$ is 2-piperidinyl;
$R_2$, $R_3$, $R_4$, and $R_5$ are each H; and
$R_6$ through $R_{10}$ are each hydrogen.

In another embodiment, the present invention provides a piperidine-flavan alkaloid compound of formula (I), namely kinkéloid $A_2$, or a pharmaceutically acceptable salt thereof, wherein:
$R_2$ is 2-piperidinyl;
$R_1$, $R_3$, $R_4$, $R_5$ are each H; and
$R_6$ through $R_{10}$ are each hydrogen.

In another embodiment, the present invention provides a piperidine-flavan alkaloid compound of formula (I), namely kinkéloid $B_1$, or a pharmaceutically acceptable salt thereof, wherein:
$R_1$ is 2-piperidinyl;
$R_2$, $R_3$, and $R_5$ are each H;
$R_4$ is OH;
$R_6$ through $R_{10}$ are each hydrogen.

In another embodiment, the present invention provides a piperidine-flavan alkaloid compound of formula (I), namely kinkéloid $B_2$, or a pharmaceutically acceptable salt thereof, wherein:
$R_2$ is 2-piperidinyl,
$R_1$, $R_3$, and $R_5$ are each H;
$R_4$ is OH;
$R_6$ through $R_{10}$ are each hydrogen.

In another embodiment, the present invention provides a piperidine-flavan alkaloid compound of formula (I), namely kinkéloid $C_1$, or a pharmaceutically acceptable salt thereof, wherein:
$R_1$ is 2-piperidinyl;
$R_2$ and $R_3$ are each H;
$R_4$ and $R_5$ are each OH;
$R_6$ through $R_{10}$ are each hydrogen.

In another embodiment, the present invention provides a piperidine-flavan alkaloid compound of formula (I), namely kinkéloid $C_2$, or a pharmaceutically acceptable salt thereof, wherein:
$R_2$ is 2-piperidinyl;
$R_1$ and $R_3$ are each H;
$R_4$ and $R_5$ are each OH;
$R_6$ through $R_{10}$ are each hydrogen.

In another embodiment, the present invention provides a piperidine-flavan alkaloid compound of formula (I), namely kinkéloid $D_1$, or a pharmaceutically acceptable salt thereof, wherein:
$R_1$ is 2-piperidinyl;
$R_2$, $R_3$, $R_4$, and $R_5$ are each OH;
$R_6$ through $R_{10}$ are each hydrogen.

In another embodiment, the present invention provides a piperidine-flavan alkaloid compound of formula (I), namely kinkéloid $D_2$, or a pharmaceutically acceptable salt thereof, wherein:
$R_2$ is 2-piperidinyl;
$R_1$, $R_3$, $R_4$, and $R_5$ are each OH; and
$R_6$ through $R_{10}$ are each hydrogen.

In another aspect the present invention provides a pharmaceutical composition derived from a species of the kinkéliba (*Combretum micranthum*) family, the composition comprising at least one piperidine-flavan alkaloid compound of formula (I):

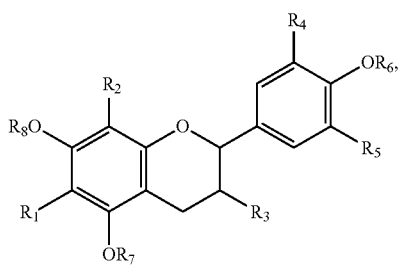

(I)

or a pharmaceutically acceptable salt thereof, wherein:
one of $R_1$ and $R_2$ is hydrogen, and the other of $R_1$ and $R_2$ is an optionally substituted 2-piperidinyl group characterized by formula (A):

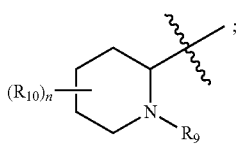

n is 0, 1, 2, or 3;

$R_3$, $R_4$ and $R_5$ are each independently selected from the group consisting of hydrogen, hydroxyl, and $C_1$-$C_4$ alkoxy;

$R_6$, $R_7$, and $R_8$ are each independently hydrogen, $C_1$-$C_4$ alkyl, or $R_{11}C(O)$—;

$R_9$ is hydrogen, $C_1$-$C_4$ alkyl, or $R_{12}C(O)$—;

$R_{10}$ at each occurrence is independently hydrogen, $C_1$-$C_4$ alkyl, or oxo (=O);

$R_{11}$ is hydrogen or $C_1$-$C_4$ alkyl; and $R_{12}$ is hydrogen, $C_1$-$C_4$ alkyl, or $OR_{11}$.

In one embodiment, the present invention provides a pharmaceutical composition derived from a species of the kinkéliba (*Combretum micranthum*) family, the composition comprising at least one piperidine-flavan alkaloid compound of formula (I), wherein:

$R_1$ is 2-piperidinyl; and $R_2$ is hydrogen.

In another embodiment, the present invention provides a pharmaceutical composition derived from a species of the kinkéliba (*Combretum micranthum*) family, the composition comprising at least one piperidine-flavan alkaloid compound of formula (I), wherein:

$R_1$ is hydrogen; and $R_2$ is 2-piperidinyl.

In another embodiment, the present invention provides a pharmaceutical composition derived from a species of the kinkéliba (*Combretum micranthum*) family, the composition comprising at least one piperidine-flavan alkaloid compound of formula (I), wherein $R_6$ through $R_{10}$ are each hydrogen.

In another embodiment, the present invention provides a pharmaceutical composition derived from a species of the kinkéliba (*Combretum micranthum*) family, the composition comprising at least one piperidine-flavan alkaloid compound of formula (I), wherein the piperidine-flavan alkaloid compound is selected from the group consisting of kinkéloids $A_1$, $A_2$, $B_1$, $B_2$, $C_1$, $C_2$, $D_1$, and $D_2$.

In another aspect the present invention provides a method of separating piperidine flavan alkaloids from leaves of *Combretum micranthum* (fam. Combretaceae), commonly known as kinkéliba, comprising extracting the leaves with one or more organic solvents.

In a preferred embodiment, the present invention provides a method of separating piperidine flavan alkaloids from leaves of *Combretum micranthum* (fam. Combretaceae), commonly known as kinkéliba, comprising extracting the leaves with a $C_1$-$C_4$ alkyl alcohol, more preferably methanol or ethanol.

In another aspect the present invention provides a method for preparing total piperidine flavan alkaloids (TPFA) from the leaves of *Combretum micranthum*, comprising:

a) extracting the leaves with an organic solvent to form a crude extract; and b) treating the crude extract with at least one of the following methods:

i) solvent fractionation using solvent systems having different polarity, ii) acid-base precipitation, iii) acid-base precipitation in combination with extraction by an organic solvent, and iv) acid-base precipitation in combination with a solvent fractionation.

In one preferred embodiment, the present invention provides a method for preparing total piperidine flavan alkaloids (TPFA) from the leaves of *Combretum micranthum*, wherein said organic solvent in step a) is an alcohol.

In another preferred embodiment, the present invention provides a method for preparing total piperidine flavan alkaloids (TPFA) from the leaves of *Combretum micranthum*, wherein said organic solvent in step a) is ethanol or methanol.

In another preferred embodiment, the present invention provides a method for preparing total piperidine flavan alkaloids (TPFA) from the leaves of *Combretum micranthum*, wherein said solvent systems in method i) comprises at least one non-polar solvent and at least one polar solvent.

In another preferred embodiment, the present invention provides a method for preparing total piperidine flavan alkaloids (TPFA) from the leaves of *Combretum micranthum*, wherein the acid-base precipitation in said method ii), iii) or iv) comprises steps of (a) dissolving the crude extract with an acidic aqueous solution; (b) filtering to remove insoluble nonpolar components; and (c) adjusting pH of the filtrate solution with a base so that precipitates are formed.

In another preferred embodiment, the present invention provides a method for preparing total piperidine flavan alkaloids (TPFA) from the leaves of *Combretum micranthum*, wherein said organic solvent in method ii) comprises an alcohol, more preferably n-butanol.

In another preferred embodiment, the present invention provides a method for preparing total piperidine flavan alkaloids (TPFA) from the leaves of *Combretum micranthum*, wherein said solvent fractionation in method iii) comprises using at least one chlorinated hydrocarbon and one alcohol, more preferably said chlorinated hydrocarbon being chloroform, and said alcohol being n-butanol.

In another preferred embodiment, the present invention provides a method for preparing total piperidine flavan alkaloids (TPFA) from the leaves of *Combretum micranthum*, further separating the kinkéloid alkaloid compounds by silica gel chromatography.

In another aspect the present invention provides a composition comprising an enriched TPFA extract derived from the leaves of *Combretum micranthum*.

In another aspect the present invention provides a method for treatment of a disease or condition related to glucose metabolism, comprising administering to a subject in need thereof a therapeutically effective amount of any piperidine-flavan alkaloid compound or composition thereof described above.

In one embodiment, the present invention provides a method for treatment of a disease or condition related to glucose metabolism, comprising administering to a subject in need thereof a therapeutically effective amount of any piperidine-flavan alkaloid compound or composition thereof described above, wherein said treatment has an effect selected from the group consisting of:

i) lowering acute blood glucose level;

ii) lowering the basal glucose level;

iii) improving glucose tolerance and glucose metabolism;

iv) lowering insulin level; and v) lowering the enzyme that is necessary for the production of glucose in the liver.

In another aspect the present invention provides a method for treatment of a disease or condition related to glucose metabolism, comprising administering to a subject in need thereof a therapeutically amount of TPFA derived from leaves of *Combretum micranthum* (fam. Combretaceae).

In another aspect the present invention provides use of a piperidine-flavan alkaloid compound as described above for manufacture of a medicament for treatment of a disease or condition related to glucose metabolism.

In yet another aspect the present invention provides use of a total piperidine-flavan alkaloid (TPFA) extract derived from the leaves of *Combretum micranthum* (fam. Combretaceae), for manufacture of a medicament for treatment of a disease or condition related to glucose metabolism.

Preparation of Crude Extract

Total crude extract of the kinkeliba leaves was prepared by different methods of aqueous ethanol extraction and methanol extraction. Sun-dried kinkéliba leaves from Leen, Pout, Senegal (near Thiès) were ground to a fine powder with a Perten Laboratory Mill 3100. The kinkéliba leaves were extracted twice with 100% ethanol and a third time with 80% ethanol (v/v) by maceration for 24 hours (Extraction Method I) or extracted three times with 100% methanol by reflux for 2 hrs (Extraction Method II). Each step was tested by LC-MS to ensure a complete extraction, and after 3 extractions, the level of alkaloids had dropped to 10% of the initial amount. The filtrations from both extraction methods were dried giving a total weight of 24.26% and 35.27% using aqueous ethanol extraction and methanol extraction, respectively, from the starting material.

Procedures for Preparing TPFA:

TPFA was prepared by several methods including, but not limited to, solvent fractionation using different polar solvent systems, acid-base precipitation, acid-base precipitation with n-butanol extraction and acid-base precipitation with chloroform and n-butanol fractionation. During solvent fractionation, the crude extract was dissolved in water and partitioned between hexane, chloroform, ethyl acetate, and n-butanol, along with the remaining water fraction. LC-MS analysis indicated that the alkaloids were focused in the n-butanol fraction. During acid-base precipitation, the crude extract was dissolved in 3% acetic acid in water and filtered by vacuum to separate the non-polar components or non-alkaloids that did not dissolve. The acidic solution was brought from pH 3 to pH 9 by the addition of $NH_4OH$ (38% in water) and the solution was allowed to precipitate and settle for 60 min before filtering by vacuum. The filtrate was collected and washed with distilled water until it ran neutral while the precipitate was dissolved in methanol and dried to obtain the total alkaloid. During acid-base precipitation with n-butanol extraction, the crude extract was dissolved in 3% Acetic Acid in water and filtered by vacuum to separate the non-polar components that did not dissolve. The acidic solution was brought from pH 3 to pH 9 by the addition of $NH_4OH$ (38% in water) and the solution was allowed to precipitate and settle for 60 min before extraction with n-butanol to obtain the total alkaloids. During acid-base precipitation with chloroform and n-butanol fractionation, the crude extract was then dissolved in 3% Acetic Acid in water and filtered by vacuum to separate the non-polar components that did not dissolve. The acidic solution was brought from pH 3 to pH 9 by the addition of $NH_4OH$ (38% in water) and the solution was allowed to precipitate and settle for 60 min before fractionation with chloroform and n-butanol. The total alkaloids were focused in n-butanol part.

The invention is described more fully by way of the following non-limiting examples.

Example 1

The First Extraction Procedure

Air-dried kinkéliba leaves, 1.04 kg, were extracted using above method (Extraction Method I) to obtain 252.3 g crude extract. The extract was then dissolved in water and partitioned between hexane (3×1.8 L), chloroform (3×1.8 L), ethyl acetate (3×2 L), and n-butanol (3×1.5 L), with the remaining water fraction totaling approximately 1.5 L. It was determined by LC-MS that the alkaloids were focused in the n-butanol fraction with a total weight of 80.66 g calculating to 7.75% from the starting materials. This fraction has been applied for further separation of the pure flavan alkaloids and biological study.

Example 2

The Second Extraction Procedure

Air-dried kinkéliba leaves, 98.39 g, were extracted using above method (Extraction Method II) to obtain 34.7 g crude extract. The extract was then dissolved in approximately 800 mL of 3% acetic acid in water and filtered by vacuum to separate the non-polar components or non-alkaloids that did not dissolve. The acidic solution was brought from pH 3 to pH 9 by the addition of $NH_4OH$ (38% in water) and the solution was allowed to precipitate and settle for 60 min before filtering by vacuum. The filtrate was collected and washed with distilled water until it ran neutral while the precipitate was dissolved in methanol and dried. The total alkaloid extract weighed 10.8840 g calculating to 11.06% from the starting materials. All the steps, from the total extract to the total alkaloid extract were calibrated to the same concentration and analyzed by LC-MS to confirm the total alkaloid extraction technique.

Example 3

The Third Extraction Procedure

Air-dried kinkéliba leaves, 102.93 g, were extracted using above method (Extraction Method II) to obtain 36.3 g crude extract. The extract was then dissolved in approximately 800 mL of 3% Acetic Acid in water and filtered by vacuum to separate the non-polar components that did not dissolve. The acidic solution was brought from pH 3 to pH 9 by the addition of $NH_4OH$ (38% in water) and the solution was allowed to precipitate and settle for 60 min before extraction with n-butanol (3×1 L) to extract the precipitated alkaloids. The total alkaloid fraction was dried and weighed 17.85 g calculating to 17.34% from the starting materials. All the steps, from the total extract to the total alkaloid extract were calibrated to the same concentration and analyzed by LC-MS to confirm the total alkaloid extraction technique.

Example 4

The Fourth Extraction Procedure

Air-dried kinkéliba leaves, 98.68 g, were extracted using above method (Extraction Method II) to obtain 34.8 g crude extract. The extract was then dissolved in approximately 800 mL of 3% Acetic Acid in water and filtered by vacuum to separate the non-polar components that did not dissolve. The acidic solution was brought from pH 3 to pH 9 by the addition of $NH_4OH$ (38% in water) and the solution was allowed to precipitate and settle for 60 min before fractionation with chloroform (3×1 L) and n-butanol (3×1 L). The total alkaloid fraction of n-butanol part was dried to obtain 11.4450 g calculating to 11.60% from the starting materials. All the steps, from the total extract to the total alkaloid extract were calibrated to the same concentration and analyzed by LC-MS to confirm the total alkaloid extraction technique.

Figure 2:
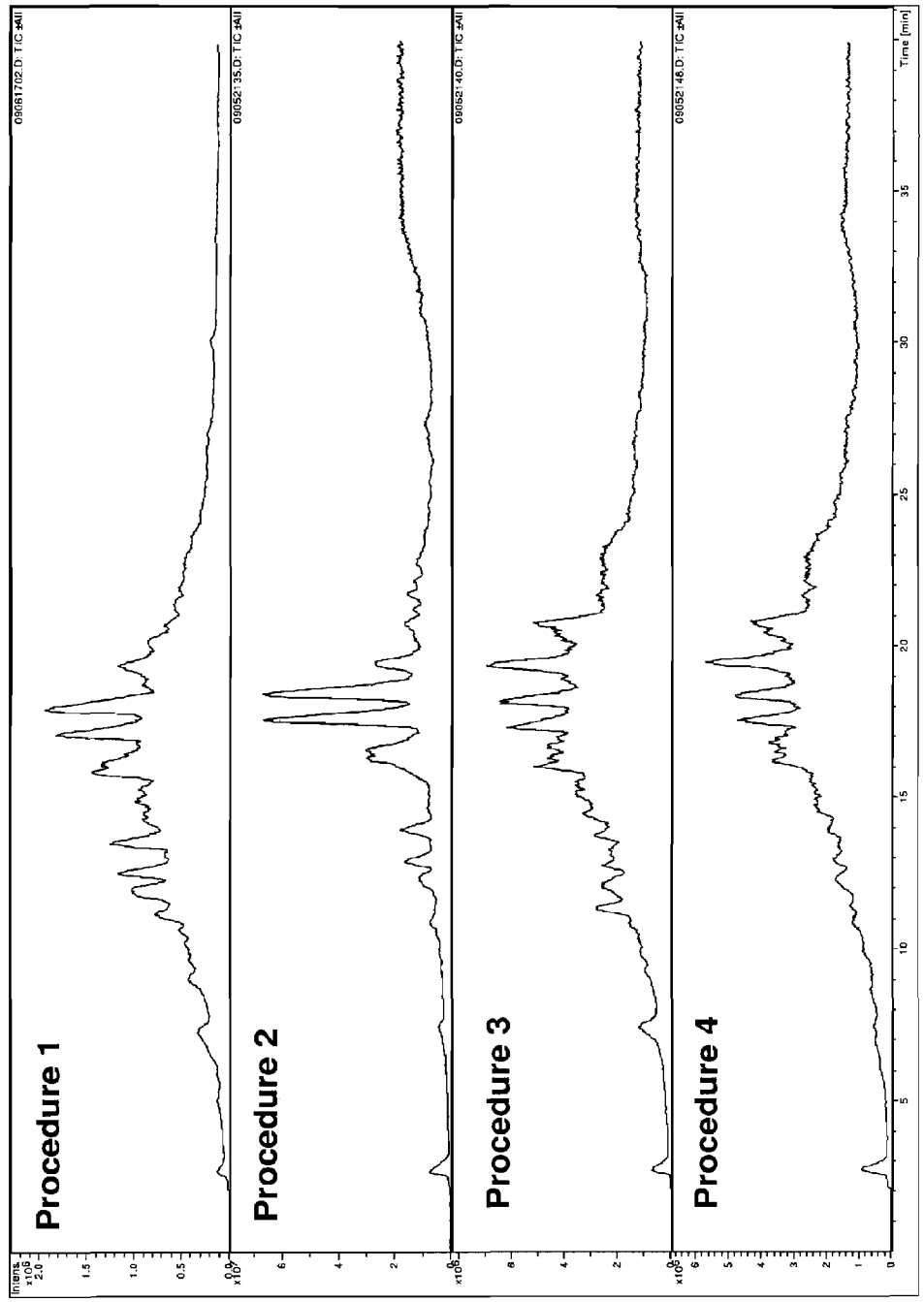
FIG. 2 illustrates MS total ion chromatograms (TIC) of total piperidine flavan alkaloids prepared from 4 procedures showing the major peaks of Kinkéloid A, B, C and D.
Figure 3:
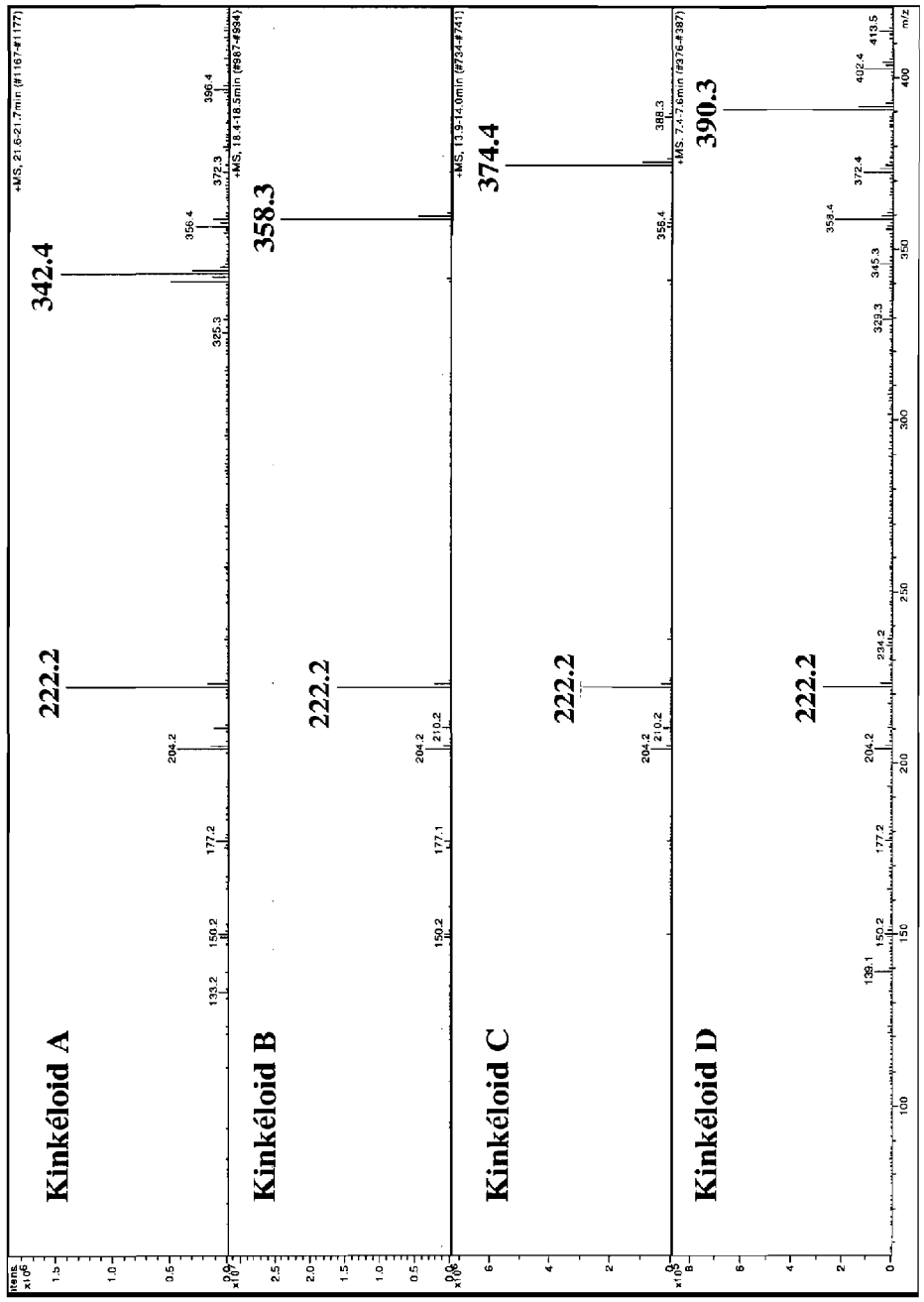
FIG. 3 illustrates MS spectra of the 4 piperidine flavan alkaloids, Kinkéloid A, B, C and D.

FIG. 2 illustrates the chemical profile of the total flavan alkaloids prepared by the above 4 procedures using LC-MS, and FIG. 3 shows the total ion MS spectra of the 4 flavan alkaloids, Kinkéloid A, Kinkéloid B, Kinkéloid C and Kinkéloid D.

Example 5

Purification of the Piperidine Flavan Alkaloids

The total alkaloid fractions were cleaned up and concentrated by running the fractions through a Sephadex LH-20 column, hydration and elution with 100% methanol. The eluted fractions from the Sephadex column were analyzed by LC-MS and the fractions that contain only alkaloids were combined and dried, calculating to approximately 32.07% of the starting material. The concentrated alkaloid mixture was separated into the separated alkaloids by preparative HPLC with a Microsorb C18 column (Varian, 10 µm, 41.4×250 mm). The mobile phase was 0.1% formic acid in water (A) and in methanol (B) at a gradient of 10% B at 0 min, 10% B at 20 min, 60% B at 170 min, and 60% at 200 min. The flow rate was set to 18 mL/min and the fractions were collected at 1 min/tube from 50 to 170 min following injection. The eluted fractions were analyzed by LC-MS and the appropriate fractions were combined and dried to give 3 of flavan alkaloids, Kinkéloid B, Kinkéloid C, and Kinkéloid D (FIG. 1). Kinkéloid A, the alkaloid in lowest concentration, could not be collected separate from B due to peak tailing, so a fraction containing both Kinkéloid A & B was separated by preparative TLC with silica at 1000 µm thickness and a developing solvent of 20% methanol in chloroform plus 0.1% triethylamine. The Kinkéloid A sample was cleaned up by analytical LC with an Inertsil column (ODS-3, 3 µm, 4.6×250 mm). The mobile phase was 0.1% formic acid in water (A) and in methanol (B) at a gradient of 20% B at 0 min, 50% B at 20 min, and 50% at 25 min at a flow rate of 0.8 mL/min. The eluted fractions were combined and dried to give the 4th new type of flavan alkaloid, Kinkéloid A (FIG. 1).

Example 6

Structural Elucidation of the Piperidine Flavan Alkaloids

The spectroscopic assignments of all four kinkéloid structures (FIG. 1) are listed in Table 1, without differentiation between C-6 and C-8.

TABLE 1

$^1$H and $^{13}$C NMR spectral data of the compounds shown below. [δ in ppm from TMS, multiplicities and J values (Hz) are given in parentheses]

| Carbon | Kinkéloid A $R_1, R_2, R_3 = H$ $^1$H | $^{13}$C | Kinkéloid B $R_1 = OH$, $R_2, R_3 = H$ $^1$H | $^{13}$C | Kinkéloid C $R_1, R_2 = OH$, $R_3 = H$ $^1$H | $^{13}$C | Kinkéloid D $R_1, R_2, R_3 = OH$ $^1$H | $^{13}$C |
|---|---|---|---|---|---|---|---|---|
| C-2 | 5.0† | 79.58 | 5.0† | 79.57 | 4.9† | 79.58 | 5.0† | 80.66 |
| C-3 | 2.13 (m) 1.88 (m) | 30.45 | 2.13 (br d) 1.87 (m) | 30.48 | 1.89 (m) 2.09 (m) | 30.46 | 3.34 (s) | 66.76 |
| C-4 | 2.64 (m) | 20.31 | 2.62 (dq, 10.8, 9.3) | 20.11 | 2.60 (dq, 15.8, 10.1) | 20.03 | 2.81 (dq, 16.8, 4.4, 2.3) | 29.48 |
| C-5 | | 155.87 | | 155.65 | | 155.62 | | 155.96 |
| C-6/8 | 6.06 (s) | 96.05 | 6.07 (s) | 96.03 | 6.06 (s) | 96.01 | 6.08 (s) | 96.51 |
| C-7 | | 155.18 | | 155.00 | | 155.07 | | 154.47 |
| C-8/6 | | 103.06 | | 102.96 | | 102.97 | | 100.82 |
| C-9 | | 158.44 | | 158.03 | | 157.96 | | 158.71 |
| C-10 | | 103.12 | | 103.08 | | 103.12 | | 103.04 |
| C-1' | | 133.92 | | 134.59 | | 134.02 | | 133.98 |
| C-2' | 6.80 (d, 7.8) | 128.45 | 6.72 (dt, 10.3, 2.1) | 118.72 | 6.42 (s) | 106.16 | 6.51 (s) | 107.04 |
| C-3' | 7.24 (d, 7.8) | 116.32 | 6.78 (dd, 8.5, 1.8) | 116.23 | | 147.15 | | 147.03 |
| C-4' | | 158.00 | | 146.49 | | 133.90 | | 131.10 |
| C-5' | 7.24 (d, 7.8) | 116.32 | | 146.24 | | 147.15 | | 147.03 |
| C-6' | 6.80 (d, 7.8) | 128.45 | 6.85 (dd, 8.5, 1.8) | 114.41 | 6.42 (s) | 106.16 | 6.51 (s) | 107.04 |
| C-1" | 4.52 (d, 12.3) | 54.78 | 4.54 (d, 12.4) | 54.79 | 4.56 (d, 11.1) | 54.76 | 4.62 (dd) | 54.89 |
| N—H | 8.39 (br s) | | 8.46 (br s) | | 8.46 (br s) | | 8.42 (s) | |
| C-3" | 3.84 (br d) 2.96 (t, 11.1) | 46.84 | 3.4 (br d) 2.97 (t, 9.3) | 46.82 | 2.98 (br s) | 46.83 | 3.39 (d, 11.4) 3.01 (t, 9.8) | 46.88 |
| C-4" | 1.88 (m) 1.60 (m) | 23.54 | 1.87 (m) 1.62 (m) | 23.53 | 1.89 (m) 1.62 (m) | 23.54 | 1.96 (m) 1.70 (m) | 23.56 |

TABLE 1-continued $^1$H and $^{13}$C NMR spectral data of the compounds shown below. [δ in ppm from TMS, multiplicities and J values (Hz) are given in parentheses]

| Carbon | Kinkéloid A $R_1, R_2, R_3 = H$ | | Kinkéloid B $R_1 = OH$, $R_2, R_3 = H$ | | Kinkéloid C $R_1, R_2 = OH$, $R_3 = H$ | | Kinkéloid D $R_1, R_2, R_3 = OH$ | |
|---|---|---|---|---|---|---|---|---|
| | $^1$H | $^{13}$C | $^1$H | $^{13}$C | $^1$H | $^{13}$C | $^1$H | $^{13}$C |
| C-5" | 1.88 (m) 1.60 (m) | 24.26 | 1.87 (m) 1.62 (m) | 24.23 | 1.89 (m) 1.62 (m) | 24.24 | 1.96 (m) 1.70 (m) | 24.31 |
| C-6" | 2.28 (m, 13.3) 1.88 (m) | 29.53 | 2.31 (m, 10.8) 1.87 (m) | 29.53 | 2.27 (m) 1.89 (m) | 29.57 | 2.31 (m) 1.96 (m) | 29.31 |

†peak obscured by water impurity

The MS spectra of the four kinkéloids (FIG. 3) illustrates the molecular weights to be 341, 357, 373 and 389, indicating a series of compounds that differ by a single hydroxyl in each case with the oxygen accounting for the 16 mass unit difference. At the outset, from HRMS, two possible formulas were deliberated for kinkéloid B from HRMS, $C_{20}H_{23}NO_5$ and $C_{18}H_{21}N_4O_4^+$, but the positive ion ESI-MS gives an $[M+H]^+$ ion at m/z 358 which would not be possible for a positively charged compound. This leaves $C_{20}H_{23}NO_5$ as the molecular formula of kinkéloid B with kinkéloid A, $C_{20}H_{23}NO_4$, kinkéloid C, $C_{20}H_{23}NO_6$, and kinkéloid D, $C_{20}H_{23}NO_7$.

The skeleton was not easily determined because the samples isolated were still mixtures of isomers, both structural, C-6 and C-8 attachment of the piperidine, and stereoisomers at both chiral centers (or three chiral centers in the case of kinkéloid D). The initial analysis of the $^{13}$C spectrum for kinkéloid B yielded an oxygenated methine, at 79.57 ppm, as well as an oxygenated methyl or nitrogenated methine, at 54.79 ppm. Nine signals were found in the unsaturated/aromatic range, 96.03-146.49 ppm and three more signals are compatible with oxygenated aromatic carbons from 155.00 to 158.03 ppm. Finally, a collection of five saturated carbons were found between 20 and 30 ppm and a signal at 46.82 ppm that could be a methylene attached to nitrogen. The proton spectrum showed a collection of messy signals, integrating to 12H, in the range of 1.5-4.0 ppm, a doublet at 4.54 ppm, 1H, a singlet at 6.07 ppm, 1H, a pair of doublets of doublets at 6.75 ppm, 2H, and a doublet at 6.85 ppm, 1H.

The assistance of 2-D spectra, HSQC, COSY and HMBC, was required to connect the flavan skeleton and piperidine substituent in a manner reasonable to fit the data. According to the HSQC spectrum, the three protons (dd at 6.72 and 6.78 ppm and d at 6.85 ppm) correlated to the three aromatic carbons from 114 to 118 ppm. This, with the splitting pattern in the proton spectrum, indicated a 3,4-dihydroxy phenyl substituent. In keeping with the molecular formula $C_{20}H_{23}NO_5$, a dihydroxy phenyl ring leaves three oxygens not yet accounted for as well as six more aromatic carbons and the structure is now comparable to 3',4',5,7-tetrahydroxyflavan. Due to the different chemical environment between C-6 and C-8 of the flavan and alkaloid NMR signals, a flavan structure with a nitrogen-containing substituent attached to ring A was explored. The COSY spectrum shows the saturated carbons between 20 and 30 ppm all seem to coordinate with each other but a closer look, combined with HSQC assignments, separates the three saturated carbons of the flavan from the five saturated carbons of the piperidine. The protons at 1.87 and 2.13 ppm (C-3) correlate to the protons at 2.62 ppm (C-4) as well as the proton at 5.0 ppm (C-2). Conversely, the protons of C-6", 1.87 and 2.31 ppm, show correlations to protons at 1.62 and 1.87 ppm (C-4" and C-5") and the doublet at 4.54 ppm (C-1"). Additionally, C-4" and -5" protons correlate to C-3" at 2.97 and 3.4 ppm. The HSQC spectrum corrected the assignment of an oxygenated methyl at 54.79 ppm to a nitrogenated methine and the downfield shift is explained by attachment to an aromatic ring. This nitrogenated methine and the nitrogenated methylene, at 46.82 ppm, can be connected to three of the five saturated $^{13}$C signals between 20 and 30 ppm (C-4", -5" and -6") composing a 2-piperindinyl substituent attached to the aromatic ring A at the methine. A similar flavonoid alkaloid compound with a 2-piperidinyl substituent was used for comparison to confirm this piperidine moiety; Ahond et al. isolated N-demethylcapitavine (10). The reported $^{13}$C spectral data matches the piperidine assignments of the kinkéloids at 53.2, 46.5, 23.5, 22.6, and 27.9 ppm for C-1"-C-6", respectively, confirming the piperidinyl moiety.

Figure 4:
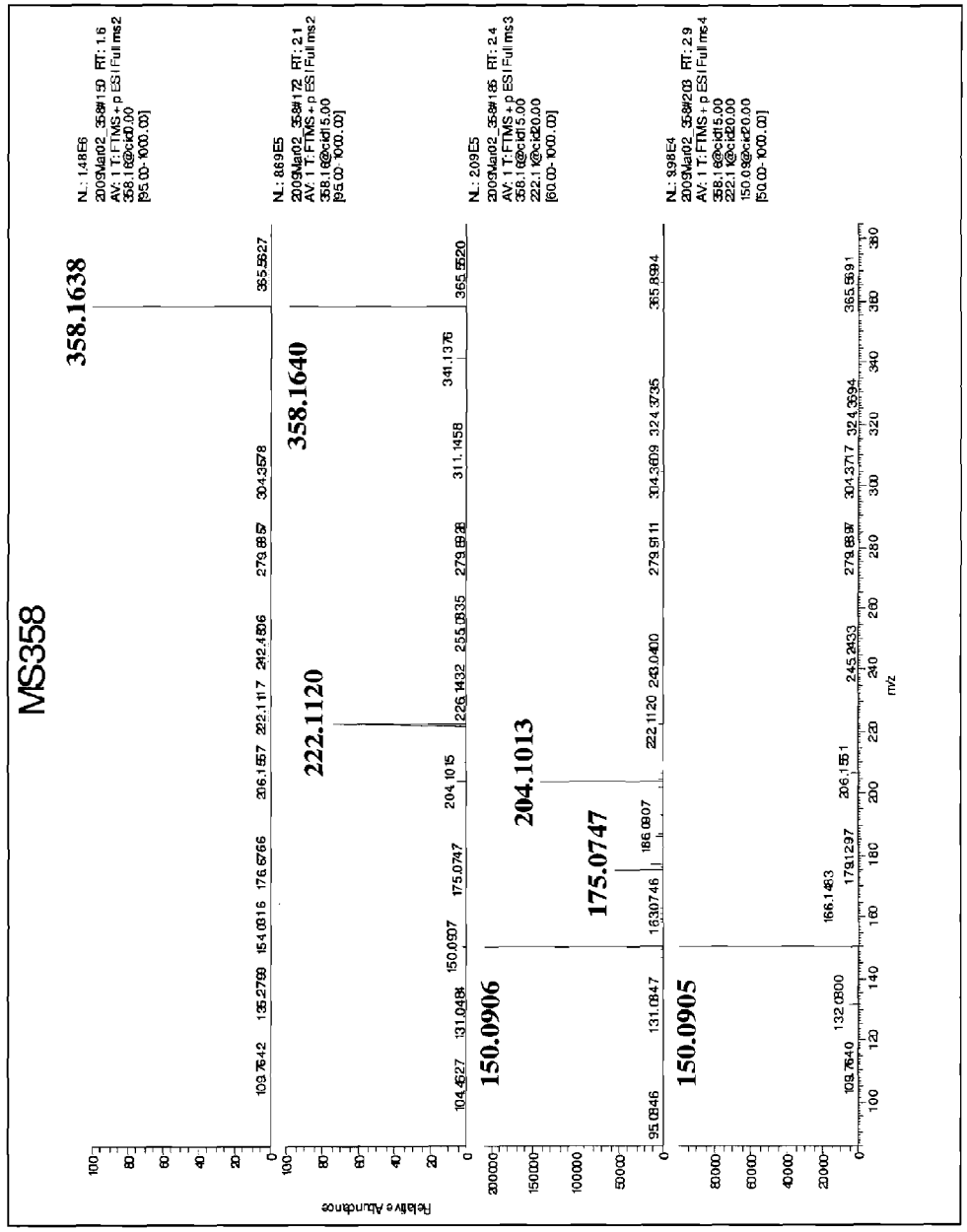
FIG. 4 illustrates High-Resolution ESI-MS spectra of Kinkéloid B
Figure 5:
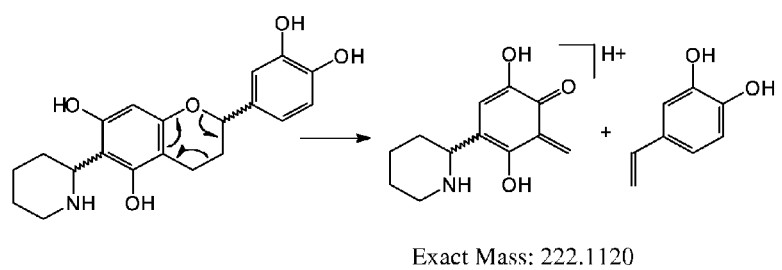
FIG. 5 illustrates proposed RDA mass spectrometric fragmentation of kinkéloid B (2)

The high-resolution mass spectrometric data of kinkéloid B (FIG. 4) was utilized to confirm placement of the piperidine on ring A of the flavan. A major fragment of m/z 222, a fragment that all the alkaloids display, was determined to be the molecular formula of $C_{12}H_{16}NO_3$ and needed to be formed by a very consistent fracture. Because all the alkaloids demonstrate this major fragment, the HRMS data of kinkéloid B can be confidently used for the elucidation of the other kinkéloids. The fragment, $C_{12}H_{16}NO_3$ at m/z 222, is attributed to the proposed mass spectrometric Retro-Diels-Alder (RDA) fragmentation for the kinkéloid structure, presented in FIG. 5, accounting for this major ion. This RDA fragmentation of the flavan is common for flavonoid compounds and strengthens the argument for the piperidine attachment to ring A. At this point the varying number of hydroxyl substituents could be assigned to ring B of the flavan, providing mono-, di-, or tri-substituted phenyls, and C-3 to give a flavan-3-ol. These hydroxyl substituents, at any of these positions, would stay with the lost fragment ensuring a consistent m/z 222 fragment in the ESI-MS spectrum of each kinkéloid.

The HMBC spectrum of kinkéloid B confirmed the connection of ring B to C-2 with correlations between the protons of C-2' and -6' and the C-2 signal and vice versa. Correlations between the protons of C-4 (2.62 ppm) and C-2, C-5 and C-10 validate the flavan structure, specifically the saturated ring C. Additionally, the HMBC spectrum revealed a couple correlations to confirm the attachment of the piperidine moiety to C-6 of the flavan structure. The proton at 4.54 ppm (C-1") shows correlations to the carbons at 29.53, 102.96 and 155.65 ppm which correspond to C-6", C-6 and C-5, respectively. This confirms, specifically H-1" to C-5, that the piperidine is attached to C-6.

An additional HMBC spectrum, on a different sample, was used to demonstrate the correlations would vary for a mixture of both structural isomers. The HMBC spectrum of this sample produces correlations between the singlet at 6.04 ppm (C-8) and the carbons at 155.10 and 158.33 ppm (C-7 and -9), confirming piperidine attachment at C-6, as well as correlations between the proton at 5.90 ppm (C-6) and the carbon at 155.75 (C-5), confirming the other isomer with attachment at C-8.

At this point, the skeleton of these alkaloid compounds is confirmed as a piperidine flavan compounds with a 2-piperidine moiety attached at C-6 and C-8. Kinkéloid C, $C_{20}H_{23}NO_6$, is the 3',4',5',5,7-pentahydroxyflavan structure; the aromatic region of ring B was simplified compared to kinkéloid B because of the identical environment for the ring B carbons and protons. The three oxygenated aromatic carbons at 147.15 (C-3'- and -5') and 133.90 ppm (C-4') and the upfield aromatic carbons at 106.16 (C-2' and -6') confirm a trihydroxy phenyl ring B.

Kinkéloid A, $C_{20}H_{23}NO_4$, is the 4',5,7-trihydroxyflavan kinkéloid; the $^1H$ and $^{13}C$ spectral shifts and observed splitting confirms this structure. The carbon signals for ring B show overlapping signals at 128.45 ppm for C-2' and -6' and 116.32 ppm for C-3' and -5' and the oxygenated aromatic carbon is at 158.00 ppm. The corresponding proton signals are a doublet for C-2' and -6' with an expected J-value of 7.8 Hz for ortho splitting and a triplet of 8.7 Hz for C-3' and -5' which can be attributed to the ortho and meta splitting.

Finally, kinkéloid D is the 3',4',5',5,7-pentahydroxyflavan-3-ol kinkéloid. This was confirmed by the $^{13}C$ spectrum displaying one less aliphatic carbon at ~20 ppm which was replaced with a carbon at ~66 ppm in the oxygenated carbon region; additionally, the aliphatic region of the $^1H$ spectrum was somewhat simplified, due to the oxygenation of C-3 and subsequent reduced splitting. A singlet at 3.34 ppm corresponded to the oxygenated proton at C-3, this then adjusts the proton and carbon signals for C-4.

Example 7

Anti-Diabetic Effects of TPFA

All animal experiments were performed according to procedures approved by the Rutgers Institutional Animal Care and Use Committee. Ten-week-old male C57BL/6J mice were purchased from the Jackson Laboratory (Bar Harbor, Me.) and maintained on a high-fat diet containing 60% fat-derived calories (D12492, Research Diets, New Brunswick, N.J.) with 12 hr light and dark cycles. The animals were randomized into 4 groups of 10 animals each. The control group was gavaged daily with the vehicle solution alone (5% DMSO) and three treatment groups were gavaged with 200 mg/kg of treatment of TPFA. Plasma glucose levels were measured at week 0 and 4 in sub-mandibular vein blood samples using a glucometer (Accu-Chek Advantage, Roche Diagnostics, Indianapolis, Ind.). A 6 hr fast was necessary to allow blood glucose concentrations to arrive at the basal level, plasma glucose concentrations were measured immediately before and 3 and 6 hr following the treatments of metformin and TPFA. This fasting glucose level was repeated at week 6 for each group to measure the full effect of the kinkéliba treatment on basal glucose levels. At week 7, an oral glucose tolerance test (OGTT) was performed. For OGTT, the mice were fasted overnight (16 hrs) and gavaged with 2 g/kg glucose solution. Glucose levels were measured using a glucometer at 0, 40, 80, and 130 min after glucose administration.

At the end of the study, mice were dosed with treatment solutions at four hours before they were euthanized. Liver and visceral fats were removed and weighed. The adipose tissue weights were normalized to final body weight as g/100 g body weight. A section of the liver was collected and stored at −80° C. until used; total RNA was extracted from the livers using Trizol reagent (Invitrogen), following the manufacturer's instructions. The RNA was treated with DnaseI (Invitrogen), following the manufacturer's guidelines, to remove any traces of DNA contamination. The cDNAs were synthesized with 2.5 µg of RNA for each sample, using Stratascript reverse transcriptase (Stratagene), following the manufacturer's protocol. The synthesized cDNAs were treated as samples from the cell culture for quantitative PCR to determine the expression of PEPCK in the treated animals versus the control.

For the results of the animal study, statistical analyses of the experimental observations, expressed as means±SEM, can be assumed to be one-way ANOVA followed with a Tukey's multiple means comparison test, unless otherwise indicated. Treatments were considered significantly different if $P<0.05$.

Plasma Glucose Levels.

Figure 6:
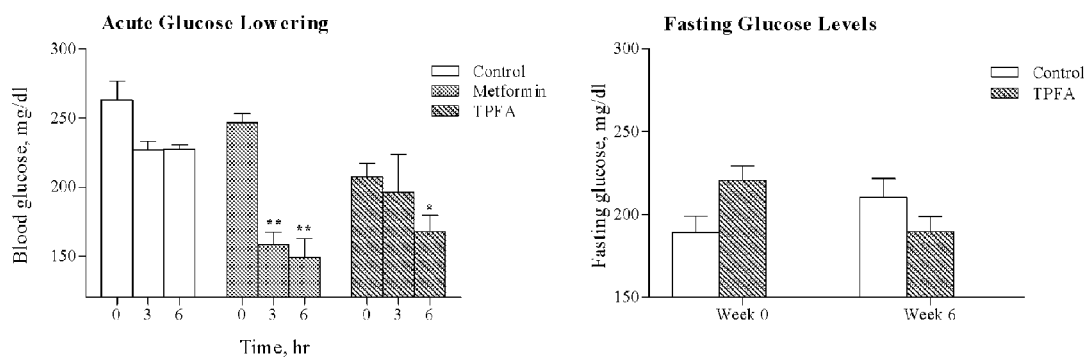
FIG. 6 illustrates the effect of TPFA on the glucose levels in mice. Left: Acute glucose experiments. Weeks 0 and 4 testing of the effect of treatments on the acute blood glucose concentration indicated a significant lowering of glucose content by the sixth hour for the TPFA group. The data represents the mean±SEM. *P<0.05, **P<0.01 (ANOVA comparison with the Control). Right: The fasting glucose levels, demonstrating a consistent increase of blood glucose concentration over the six weeks for the control but a steady decrease for the treatment group with TPFA.

The acute blood glucose levels were determined at weeks 0 and 4; there was a significant lowering of glucose levels by the sixth hour for the TPFK treated group compared to the control (FIG. 6, Left). Metformin is included here as a positive control and the data is illustrated as means±SEM, a two-way ANOVA followed by Bonferroni post test was performed with $P<0.05$ indicated.

At week 6, the ambient glucose level was measured again and the results, over the 6 weeks, demonstrated the treatments were affecting the basal glucose levels. The control group showed an increase of fasting blood glucose by 11.21% while the TPFA treated group all decreased 13.96%. The actual data (FIG. 6, Right.) shows the control group starting at the lowest blood glucose but increasing throughout the experiment while the treatment group decreases from week 0 to week 6 indicating that the TPFA treatment group effectively lowers the basal glucose level, signifying an anti-diabetic effect.

Glucose Tolerance Test.

Figure 7:
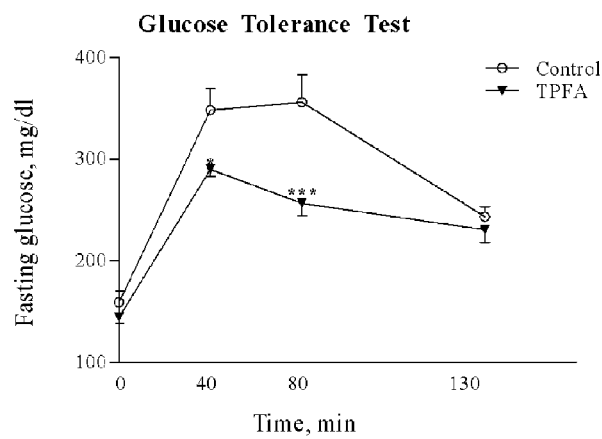
FIG. 7 illustrates the results of Glucose Tolerance Test in mice. At the conclusion of the six-week study, the oral glucose tolerance of the animals were tested to determine if the daily treatments improved the tolerance. At 40 and 80 min. following oral glucose challenge, the TPFA treated group had significantly lowered plasma glucose concentrations compared to the control. The data represents the mean±SEM. *P<0.05, ***P<0.001 (ANOVA comparison with the Control).

The oral glucose tolerance test was performed in week 7 of the experiment. The TPFA treatment group significantly improved glucose tolerance (FIG. 7) by lowering the peak, 40 min following the glucose challenge. Additionally, the glucose levels at 80 min post glucose challenge were significantly lowered when compared to the control group, another indicator of improved glucose metabolism. The curves across 130 min experiment are the values as means±SEM, a two-way ANOVA followed by Bonferroni post test was performed with $P<0.05$ and $P<0.001$ indicated.

Plasma Insulin Levels.

Figure 8:
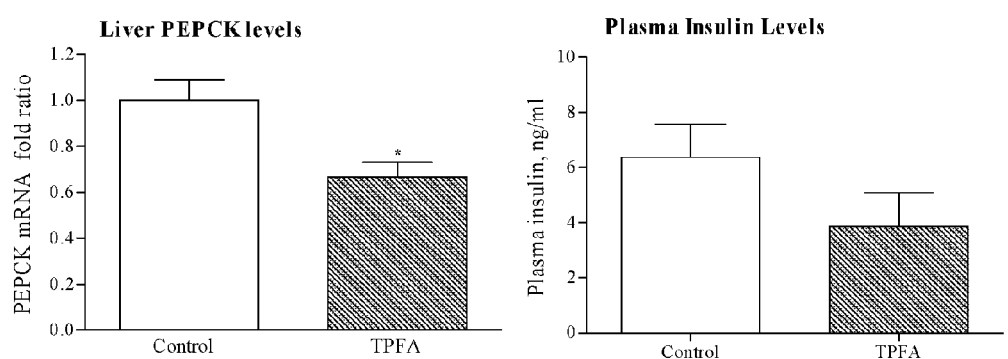
FIG. 8 illustrates the effects of TPFA on PEPCK levels in the liver and on insulin levels in plasma. Left: PEPCK levels in the liver. At the conclusion of the animal study, the PEPCK gene expression was measured in the liver tissue to determine the affect the treatments had on hepatic glucose production. The TPFA treated group demonstrated significantly lowered PEPCK levels than the control. The data represents the mean±SEM. *P<0.05 (ANOVA comparison with the Control). Right: Plasma insulin levels at the conclusion of the study, illustrating a decrease of insulin concentration for the TPFA treated group. The data represents the mean±SEM.

The plasma insulin concentrations were measured for each animal across the treatment and control groups at the conclusion of the study. The plasma collection and testing resulted in nine viable samples per group after some samples hemolyzed and one animal died in week 6. The TPFA treated group exhibits lower insulin levels than the control (FIG. 8, Right).

Gene Expression in Liver Tissue.

The liver tissue samples were tested for PEPCK gene expression to determine the actual affect of the treatment on hepatic glucose production (13, 14); a decrease in this gene in the liver indicates antidiabetic activity. The result indicates that the TPFA treated group demonstrated significantly lowered levels of PEPCK (FIG. 8). These results indicate the ability of TPFA fraction to lower the enzyme that is necessary for the production of glucose in the liver.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein. All references cited herein are incorporated by reference in their entirety herein.

REFERENCES

1. Iwu, M. M., *Handbook of African Medicinal Plants*. 1993, Florida: CRC Press, Inc. 464.
2. Kerharo, J., *Combrétacées, in La Phannacopée Sénégalaise Tranditionnelle Plantes Médicinales Et Toxiques*, J. G. Adam, Editor. 1974, Vigot Fréres: Paris. p. 341-360.
3. Le Grand, A., *Les phytotherapes anti-infectieuses de la foret-savane, Senegal(Afrique occidentale) III. un resume des substances phytochimiques et l' activite antimicrobienne de 43 species*. Journal of Ethnopharmacology, 1989. 25: p. 315-338.
4. Le Grand, A. and P. A. Wondergem, *Les phytotherapes anti-infectieuses de la foret-savane, Senegal (Afrique occidentale) I. un inventaire*. Journal of Ethnopharmacology, 1987. 21: p. 109-125.
5. D'Agostino, M., et al., *Flavonoids of Combretum micranthum*. Fitoterapia, 1990. 61: p. 477.
6. Tignokpa, M., et al., *Plantes medicinales populaires des marches de Dakar (Senegal)*. International Journal of Crude Drug Research, 1986. 24: p. 75-80.
7. Olajide, O., J. M. Makinde, and D. T. Okpako, *Evaluation of the anti-inflammatory property of the extract of Combretum micranthum G. Don. (Combretaceae)*. Inflammopharmacology, 2003. 11(3): p. 293-298.
8. Karou, D., et al., Antioxidant and antibacterial activities of polyphenols from ethnomedicinal plants of Burkina Faso. African Journal of Biotechnology, 2005. 4(8): p. 823-828.
9. Gustad, G., S. S. Dhillion, and D. Sidibe, *Local use and cultural and economic value of products from trees in the parklands of the municipality of Cinzana, Mali*. Economic Botany, 2004. 58(4): p. 578-587.
10. Ahond, A.; Fournet, A.; Moretti, C.; Philogene, E.; Poupat, C.; Thoison, O.; Potier, P., Premiers alcaloides vrais isoles de Combretacees, *Buchenavia macrophylla* Eichl. et *Buchenavia capitata* Eichl. *Bulletin de la Societe Chimique de France* 1984, 1-2, (2), 41-45.
11. WHO, Diabetes Fact Sheet. In 2008.
12. Dembinska-Kiec, A.; Mykkanen, O.; Kiec-Wilk, B.; Mykkanen, H., Antioxidant phytochemicals against type 2 diabetes. *The British Journal of Nutrition* 2008, 99, ES109-ES117.
13. Ramadoss, P.; Unger-Smith, N. E.; Lam, F. S.; Hollenberg, A. N., STAT3 targets the regulatory regions of gluconeogenic genes in vivo. *Molecular Endocrinology* 2009, 23, (6), 827-837.
14. Kim, J. H.; Bachmann, R. A.; Chen, J., Interleukin-6 and insulin resistance. *Vitamins and Hormones* 2009, 80, 613-633.

What is claimed is:

1. A piperidine-flavan alkaloid compound of formula (I):

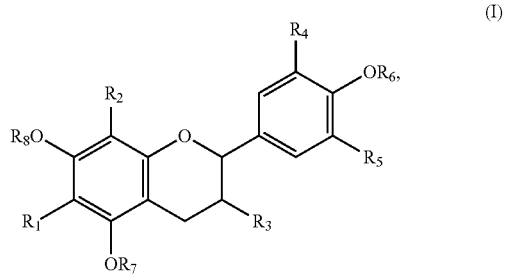

or a pharmaceutically acceptable salt thereof, wherein:
one of $R_1$ and $R_2$ is hydrogen, and the other of $R_1$ and $R_2$ is an optionally substituted 2-piperidinyl group characterized by formula (A):

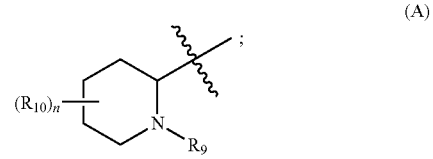

n is 0, 1, 2, or 3;
$R_3$, $R_4$ and $R_5$ are each independently selected from the group consisting of hydrogen, hydroxyl, and $C_1$-$C_4$ alkoxy;
$R_6$, $R_7$, and $R_8$ are each independently hydrogen, $C_1$-$C_4$ alkyl, or $R_{11}C(O)$—;
$R_9$ is hydrogen, $C_1$-$C_4$ alkyl, or $R_{12}C(O)$—;
$R_{10}$ at each occurrence is independently hydrogen, $C_1$-$C_4$ alkyl, or oxo (=O);
$R_{11}$ is hydrogen or $C_1$-$C_4$ alkyl; and
$R_{12}$ is hydrogen, $C_1$-$C_4$ alkyl, or $OR_{11}$.

2. The piperidine-flavan alkaloid compound of claim 1, or a pharmaceutically acceptable salt thereof, wherein $R_6$ through $R_{10}$ are each hydrogen.

3. The piperidine-flavan alkaloid compound of claim 1, namely kinkéloid $A_1$, or a pharmaceutically acceptable salt thereof, wherein:
$R_1$ is 2-piperidinyl;
$R_2$, $R_3$, $R_4$, and $R_5$ are each H; and
$R_6$ through $R_{10}$ are each hydrogen.

4. The piperidine-flavan alkaloid compound of claim 1, namely kinkéloid $A_2$, or a pharmaceutically acceptable salt thereof, wherein:
$R_2$ is 2-piperidinyl;
$R_1$, $R_3$, $R_4$, $R_5$ are each H; and
$R_6$ through $R_{10}$ are each hydrogen.

5. The piperidine-flavan alkaloid compound of claim 1, namely kinkéloid $B_1$, or a pharmaceutically acceptable salt thereof, wherein:
$R_1$ is 2-piperidinyl;
$R_2$, $R_3$, and $R_5$ are each H;
$R_4$ is OH;
$R_6$ through $R_{10}$ are each hydrogen.

6. The piperidine-flavan alkaloid compound of claim 1, namely kinkéloid $B_2$, or a pharmaceutically acceptable salt thereof, wherein:
$R_2$ is 2-piperidinyl,
$R_1$, $R_3$, and $R_5$ are each H;
$R_4$ is OH;
$R_6$ through $R_{10}$ are each hydrogen.

7. The piperidine-flavan alkaloid compound of claim 1, namely kinkéloid $C_1$, or a pharmaceutically acceptable salt thereof, wherein:
$R_1$ is 2-piperidinyl;
$R_2$ and $R_3$ are each H;
$R_4$ and $R_5$ are each OH;
$R_6$ through $R_{10}$ are each hydrogen.

8. The piperidine-flavan alkaloid compound of claim 1, namely kinkéloid $C_2$, or a pharmaceutically acceptable salt thereof, wherein:
$R_2$ is 2-piperidinyl;
$R_1$ and $R_3$ are each H;
$R_4$ and $R_5$ are each OH;
$R_6$ through $R_{10}$ are each hydrogen.

9. The piperidine-flavan alkaloid compound of claim 1, namely kinkéloid $D_1$, or a pharmaceutically acceptable salt thereof, wherein:
$R_1$ is 2-piperidinyl;
$R_2$, $R_3$, $R_4$, and $R_5$ are each OH;
$R_6$ through $R_{10}$ are each hydrogen.

10. The piperidine-flavan alkaloid compound of claim 1, namely kinkéloid $D_2$, or a pharmaceutically acceptable salt thereof, wherein:
$R_2$ is 2-piperidinyl;
$R_1$, $R_3$, $R_4$, and $R_5$ are each OH; and
$R_6$ through $R_{10}$ are each hydrogen.

11. A pharmaceutical composition derived from a species of the kinkéliba (*Combretum micranthum*) family, the composition comprising at least one piperidine-flavan alkaloid compound of formula (I):

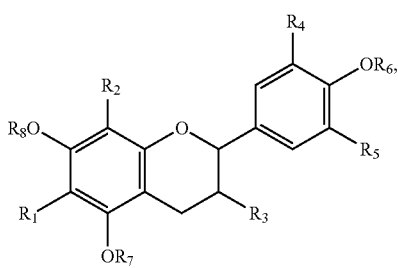

(I)

or a pharmaceutically acceptable salt thereof, wherein:
one of $R_1$ and $R_2$ is hydrogen, and the other of $R_1$ and $R_2$ is an optionally substituted 2-piperidinyl group characterized by formula (A):

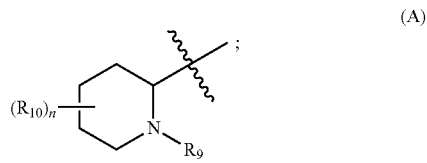

(A)

n is 0, 1, 2, or 3;
$R_3$, $R_4$ and $R_5$ are each independently selected from the group consisting of hydrogen, hydroxyl, and $C_1$-$C_4$ alkoxy;
$R_6$, $R_7$, and $R_8$ are each independently hydrogen, $C_1$-$C_4$ alkyl, or $R_{11}C(O)$—;
$R_9$ is hydrogen, $C_1$-$C_4$ alkyl, or $R_{12}C(O)$—;
$R_{10}$ at each occurrence is independently hydrogen, $C_1$-$C_4$ alkyl, or oxo (=O);
$R_{11}$ is hydrogen or $C_1$-$C_4$ alkyl; and
$R_{12}$ is hydrogen, $C_1$-$C_4$ alkyl, or $OR_{11}$.

12. The pharmaceutical composition of claim 11, wherein:
$R_1$ is 2-piperidinyl; and
$R_2$ is hydrogen.

13. The pharmaceutical composition of claim 11, wherein:
$R_1$ is hydrogen; and
$R_2$ is 2-piperidinyl.

14. The pharmaceutical composition of claim 11, wherein:
$R_6$ through $R_{10}$ are each hydrogen.

15. The pharmaceutical composition of claim 11, wherein the piperidine-flavan alkaloid compound is selected from the group consisting of kinkéloids $A_1$, $A_2$, $B_1$, $B_2$, $C_1$, $C_2$, $D_1$, and $D_2$.

16. The pharmaceutical composition of claim 12, wherein:
$R_6$ through $R_{10}$ are each hydrogen.

17. The pharmaceutical composition of claim 13, wherein:
$R_6$ through $R_{10}$ are each hydrogen.

* * * * *